United States Patent
Vogt

(10) Patent No.: US 6,669,474 B2
(45) Date of Patent: Dec. 30, 2003

(54) ANTI-ROTATIONAL INTERARCH ORTHODONTIC DEVICE

(76) Inventor: William Vogt, 3501 Freemansburg Ave., Easton, PA (US) 18045

( * ) Notice: Subject to any disclaimer, the term of this patent is extended or adjusted under 35 U.S.C. 154(b) by 97 days.

(21) Appl. No.: 10/132,313

(22) Filed: Apr. 26, 2002

(65) Prior Publication Data
US 2002/0164555 A1 Nov. 7, 2002

Related U.S. Application Data

(60) Provisional application No. 60/287,747, filed on May 2, 2001.

(51) Int. Cl.[7] ............................................... A61C 3/00
(52) U.S. Cl. ..................................................... 433/19
(58) Field of Search ............................. 433/18, 19, 21

(56) References Cited

U.S. PATENT DOCUMENTS

| | | | | | |
|---|---|---|---|---|---|
| 4,618,324 A | * | 10/1986 | Nord | ............................ | 433/19 |
| 5,697,782 A | * | 12/1997 | Klapper et al. | ............... | 433/19 |
| 5,711,667 A | | 1/1998 | Vogt | ............................. | 433/19 |
| 5,718,576 A | * | 2/1998 | Schnaitter et al. | ............. | 433/22 |
| 5,752,823 A | * | 5/1998 | Vogt | ............................. | 433/19 |
| 6,113,390 A | | 9/2000 | Sirney et al. | .................. | 433/19 |
| 6,120,289 A | * | 9/2000 | Cleary et al. | .................. | 433/22 |
| 6,322,357 B1 | * | 11/2001 | Vogt | ............................. | 433/19 |
| 6,589,051 B2 | * | 7/2003 | Cleary | .......................... | 433/19 |

* cited by examiner

Primary Examiner—Ralph A. Lewis
(74) Attorney, Agent, or Firm—Gregory J. Gore

(57) ABSTRACT

An orthodontic interarch device includes a recurve bend located adjacent a shepherd's hook or loop-type attachment that makes the anterior end of the device rotate downwardly rather than upwardly when force is applied. As the person's jaws move, a cam action against the archwire is produced that does not allow the hook or loop attachment end of the device to move above the horizontal plane of the bite as the connection rotates. The recurve bend should be a minimum of 120 degrees from the longitudinal axis of the interarch device in the backward direction. As the degree of this backward curvature approaches 210 degrees, the recurve bend further positions a hook attachment pivot point below axis of the body of the interarch device in the vertical plane. This further prevents the appliance from rotating into the bite.

11 Claims, 3 Drawing Sheets

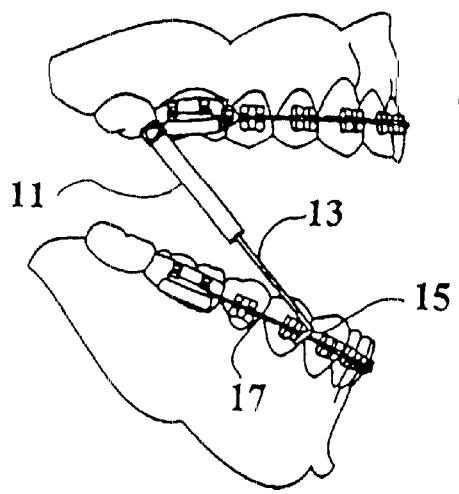
FIG. 1 (Prior Art)
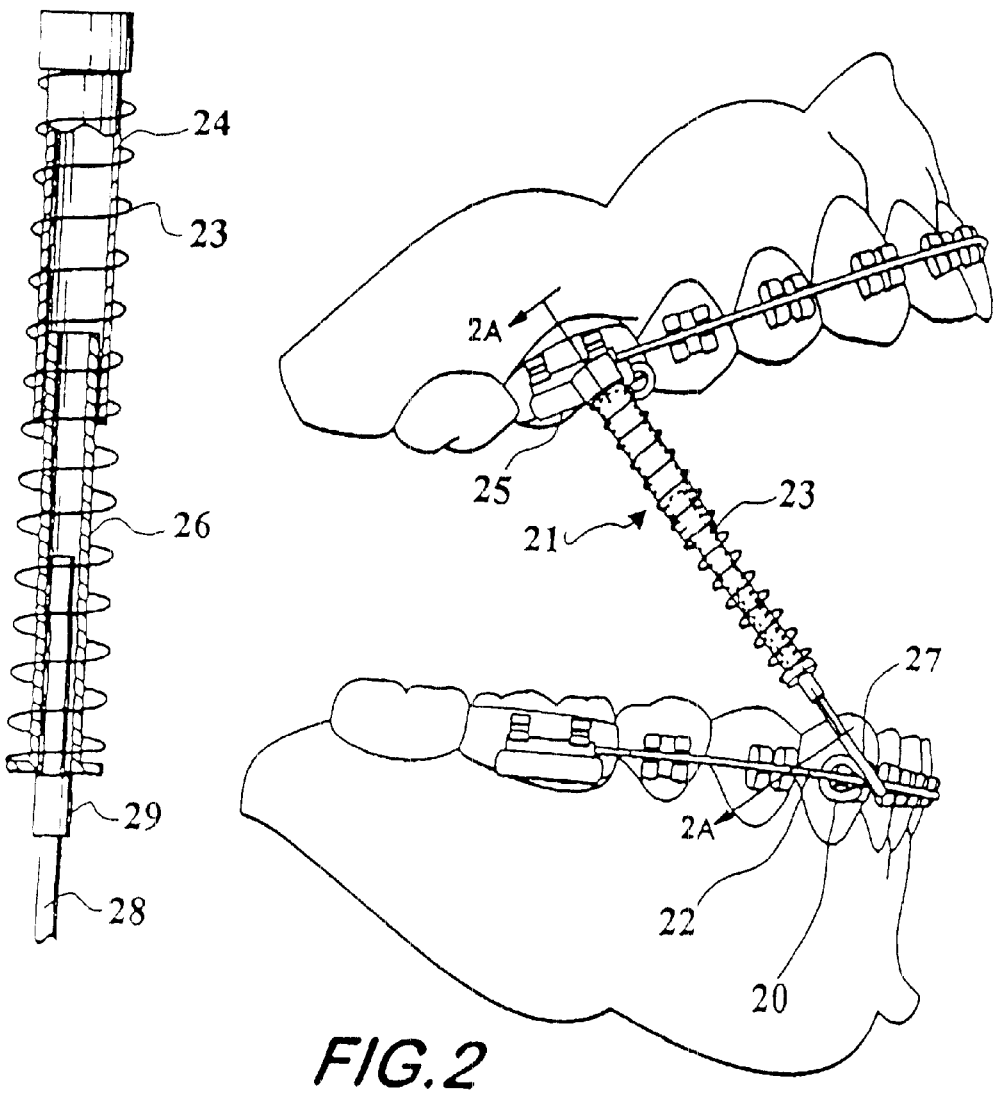
FIG. 2A
FIG. 2

ANTI-ROTATIONAL INTERARCH ORTHODONTIC DEVICE

The present application is related to provisional patent application Ser. No. 60/287,747 entitled "Anti-Rotational Bend for Interarch Orthodontic Appliances" filed on May 2, 2001, priority from which is hereby claimed.

FIELD OF THE INVENTION

The present invention relates to a means for attachment of intraoral dental or orthodontic force modules, which are used to correct or maintain the position of the upper teeth and or jaws relative to the lower teeth and or jaws.

BACKGROUND OF THE INVENTION

It is generally known in the field of dentistry, and in particular the specialty of orthodontics, to utilize rigid, one-piece or telescoping devices to position the jaws in a more favorable relation to each other or to deliver tooth moving forces between the jaws. The telescoping devices are either pushrod-and-cylinder or cylinder-within-cylinder type devices. Interarch devices are fixed directly or indirectly to devices such as orthodontic braces or are fixed to removable plates that are in turn fixed to the patient's teeth. Interarch devices can either be passive or active. An example of an active interarch device is shown in my U.S. Pat. No. 5,711,667 which is incorporated by reference as though fully set forth.

However, a problem exists with these interarch devices. When opening the mouth, an interarch device that is loosely attached to the braces about the archwire in the lower anterior region of the teeth tends to rotate upwardly in the front of the mouth toward the upper teeth. FIG. 1 illustrates how the anterior end of the pushrod of an interarch device rotates upward and into the bite when the patient opens his/her mouth. Element 11 is a cylinder and 13 is the long arm of the pushrod. Element 15 is the anterior connection of the pushrod which in this case is a hook formed in the end of the pushrod which encircles the lower archwire 17. With the structures in this position, the patient can bite on the arm of the attachment hook when he/she closes his/her mouth. This occurs because the attachment point is offset from the body a sufficient distance to enter the patent's bite when a common hook or loop attachment is employed. A bend, usually 90 degrees or less, is employed to place the axis of the hook parallel to the axis of the archwire to permit sliding movement along the archwire. However, these mechanical relations allow the unrestricted rotation about the archwire which creates the unwanted motion of the end of the pushrod into the patient's bite.

This tendency to rotate into the bite is increased when the loosely attached interarch device is active due to its having a push-spring such as an open coil spring incorporated into its design. In an active telescoping device, the nature of the activated spring is to tend to return to a state of least spring energy, (i.e. greatest length). In the case of prior art telescoping interarch devices this most extended state occurs when the device has rotated upwardly at its anterior connection. Thus, the spring forces the arm of the hook or loop attachment structure to rotate up into the area of the patient's bite.

The tendency of the interarch device to rotate upward in the anterior region can be avoided at present by two means: either rigidly fixing the anterior connection, or by moving the anterior connection point lower than the lower teeth by connecting it using an additional bypass wire that is lower than the level of the braces in the direction of the gums. In this case, when the device rotates, it is still at a level lower than the lower teeth thereby avoiding the bite. Although rigid fixation prevents the appliances from rolling into the bite, it usually limits the patient's range of jaw motion. In addition, rigid fixation usually requires many more parts and complicated design features that make both manufacturing and installation in the patient's mouth more difficult.

A loose attachment of the orthodontic appliance described above is preferred because it allows for greater freedom of motion. However, as noted above, a loose attachment encourages push-spring loaded interarch appliances to rotate into the bite because the compressed spring tends to naturally return to its uncompressed normal state (least stored energy) and thus has a tendency to move to a position of greatest extension in the unwanted upward direction. Therefore, a second solution as previously mentioned is to utilize a bypass wire which lowers the connection point of the attachment. Thus, when the interarch device does rotate, it rolls into the side of the teeth instead of the bite and this prevents the patient from biting it. But unfortunately, adding a bypass wire increases the number of parts that must be manufactured and installed. In addition, the bypass wire increases the chance of breakage by the patient when chewing and it makes the appliance more intrusive by adding to its overall bulk.

There is therefore a need in the art for an improved attachment that allows an interarch orthodontic device to be loosely attached to the patient's upper and lower teeth that is simple to manufacture and to install and does not allow the device to interfere with the patient's bite.

SUMMARY OF THE INVENTION

The present invention consists of the addition of a recurve bend located adjacent to a shepherd's hook or loop attachment of a telescoping or rigid interarch orthodontic device that makes the anterior end of the device rotate downwardly rather than upwardly when force is applied. When the device is installed onto the patient's braces the additional recurve bend in effect creates a rocker arm. As the jaws move, a cam-action against the archwire is produced that does not allow the attachment end of the device to move above the horizontal plane of the bite as the connection rotates.

For the recurve bend of the invention to create the beneficial desired cam-action, the bend should be a minimum of 120 degrees from the longitudinal axis of the interarch orthodontic device in the backward direction. As the degree of this backward curvature approaches 210 degrees, the recurve bend further positions the hook attachment pivot point below the axis of the body of the interarch device in the vertical plane. This further prevents the appliance from rotating into the bite because the position of greatest possible extension is approached as the device rotates downward instead of upward at the anterior end of the bite. An optional second offset bend in the lateral plane of no more than 60 degrees creates a second beneficial cam effect in the lateral plane.

More specifically, the applicant has invented an interarch orthodontic device for a person comprising a body including a cylinder having first attachment means affixed to an upper tooth at one end and an opening at an opposite end. A telescopic rod is slidably retained within a bore of the cylinder and the distal end of the rod extending from the cylinder includes second attachment means which provide pivotable hook-type attachment about an archwire affixed to an orthodontic appliance which in turn is affixed to a lower tooth. A recurve bend located on the rod lies adjacent the lower archwire attachment so that when a person's jaws are moved toward the closed position, contact between the sides of the hook and the archwire hold the rod away from the person's bite. Spring means may be included either surrounding the cylinder and rod or within the cylinder bore providing a resilient force bearing against the end of the rod. The recurve bend is preferably greater than 135 degrees. The posterior end of the rod can include a substantially cylindrical cavity which receives the spring means. The interarch orthodontic device may be oriented so that the attachment means at the end of the rod are oriented either anteriorly or posteriorly. Other details of the invention will be apparent from the following drawings and description of the preferred embodiment.

BRIEF DESCRIPTION OF THE DRAWINGS

FIG. 1 is a side view of an orthodontic interarch device of the prior art.

FIG. 2 is a side view of the interarch orthodontic device of the present invention.

FIG. 2A is a longitudinal cross-section taken from FIG. 2 as shown in that figure.

DESCRIPTION OF THE PREFERRED EMBODIMENT

Figure 3:
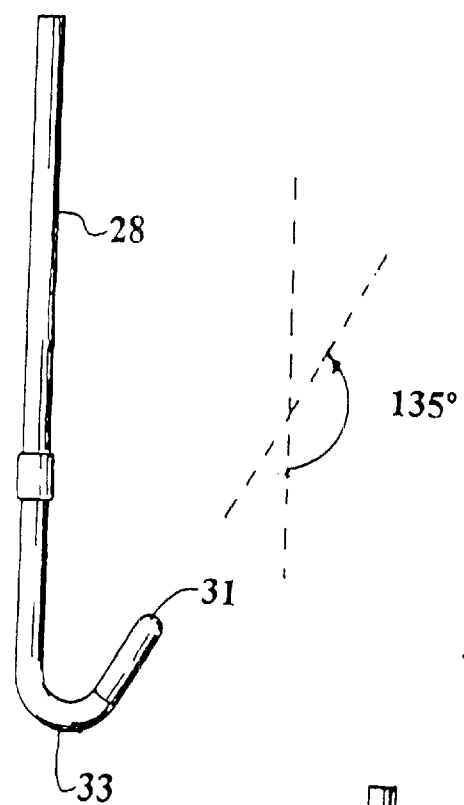
FIG. 3 is a side view of the rod of the interarch device.

Referring now to FIG. 2, the interarch device 21 of the present invention is shown connected between the patient's upper and lower teeth 25 and 27 respectively. The anterior attachment means 20 at the lower jaw is loosely fitted around the lower archwire 22 at the anterior end of the device. From this view it can be seen that the axis of the attachment loop is not parallel to the axis of the archwire. Spring means 23 operates between the ends of the device and applies a compressive force between the upper tooth 25 and lower tooth 27.

Referring now to FIG. 2A, greater detail of the telescoping mechanism of the interarch device is depicted. Spring means 23 operates between stops at the ends of upper cylinder 24 and interfitting lower cylinder 26 which bears against pushrod 28 by abutment with pushrod stop 29. It will be readily understood that by these mechanical relations that spring 23 applies a compressive force between the upper cylinder 24 and pushrod 28.

Figure 4:
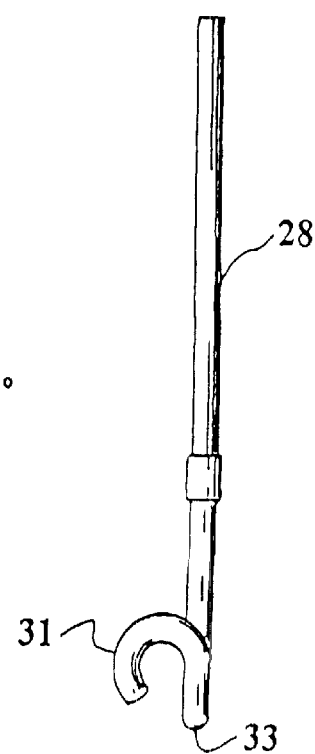
FIG. 4 is a front view of the rod shown in FIG. 3.
Figure 5:
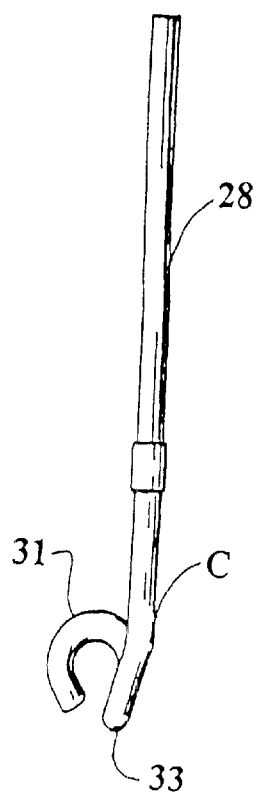
FIG. 5 is a front view of an alternate embodiment of the invention.

FIG. 3 shows the construction of pushrod 28 taken from the telescoping intraoral device of FIG. 2. A shepherd's hook 31 is formed at the end of the pushrod to form archwire attachment means as shown in FIG. 2. The attachment means, in this case a shepherd's hook, includes a recurve bend 33 of 135 degrees that provides a pivotable attachment point offset from the axis of the pushrod. The bend makes the attachment portion double-back toward the body portion of the interarch device. FIG. 4 is a side view of FIG. 2 with the same elements similarly numbered. FIG. 5 is a side view of an alternate embodiment similar to FIG. 4 that shows the inclusion of a second offset bend C in the lateral plane which further prevents pushrod upward rotation.

Figure 6:
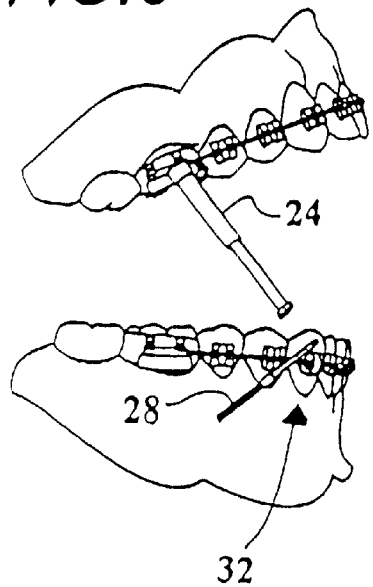
FIG. 6 is a side view of the invention in a dissembled condition.

FIG. 6 demonstrates the downward rotational bias of the invention and shows that with the recurve bend included at the attachment end 32 of the pushrod 28, the rod functions like a rocker arm that bears against the archwire. If the pushrod is positioned in the undesirable position of upward rotation in the front of the mouth, the sides of the hook which bear against the archwire force the long arm of the pushrod downward at the posterior end. It is therefore impossible to slide the pushrod into the cylinder 24 with the pushrod rotated up in the anterior because, as shown in this figure, the angle of the cylinder 24 and the angle of the pushrod 28 do not match.

Figure 7:
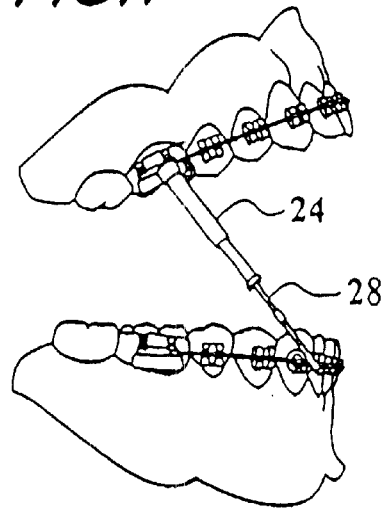
FIG. 7 is a side view of an embodiment of the invention.

FIG. 7 shows the pushrod of FIG. 6 now inserted into the cylinder. As demonstrated above, the only way this can be accomplished is with the pushrod rotated down at the front. Thus, when the pushrod 28 and the cylinder 24 are engaged, the downward angle of the posterior arm of the pushrod 28 is prevented. If the pushrod is urged to rotate upward at the anterior, further upward rotation into the bite plane is prevented by contact between the archwire and the sides of the attachment hook. These mechanical relations contrast with the prior art having a bend which places the archwire along the central axis of the hook allowing its free unrestricted rotation into the bite. The embodiment shown in FIGS. 6 and 7 may include an internal spring (not visible) within the cylinder which bears against the end of the pushrod. It should be understood that the orientation of the device shown in FIGS. 6 and 7 may be reversed so that the cylinder end is at the anterior end and the pushrod is at the posterior end.

Figure 8:
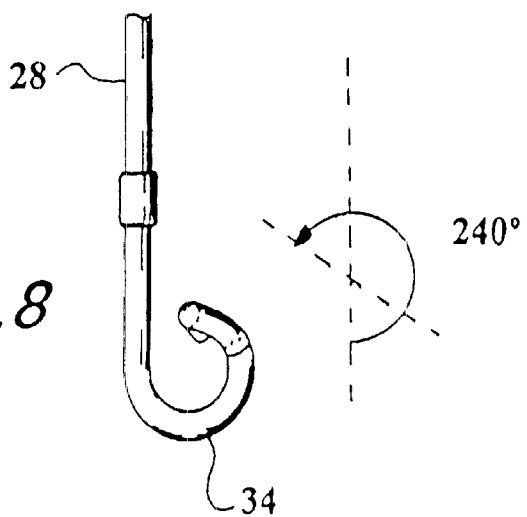
FIGS. 8, 9, and 10 are side views of alternate rod embodiments of the invention.
Figure 9:
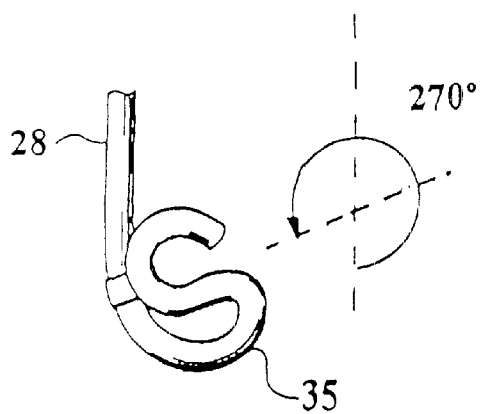
Figure 10:
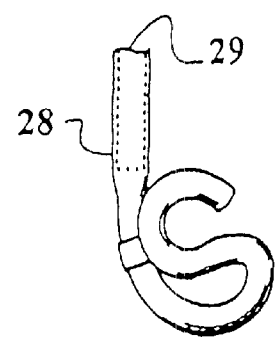

Referring now to FIGS. 8, 9, and 10, FIG. 8 shows an increased recurve bend 34 of approximately 240 degrees, and FIG. 9 illustrates an even greater bend 35 of about 270 degrees. In this case the attachment hook must be bent out away from the body so there is room to hook it onto the patient's archwire. A recurve bend of this magnitude positions the attachment pivot point below the axis of the body of the interarch device in the vertical plane. FIG. 10 is the same as FIG. 9 except that the posterior end of pushrod 28 is replaced with a cylinder 29 so that a telescoping device can have a pushrod or a second sliding cylinder surrounding the first cylinder. In this case, an internal coil spring (not shown) may be located within both cylinders. In all embodiments, the cam-action of the hook against the archwire creates a counteracting force to overcome the forces which otherwise naturally occur that would cause the interarch device to rotate upward into the patient's bite at its anterior point of attachment.

From the foregoing description of the invention it will be apparent that the objects of the invention have been achieved. The addition of the above-described bends at the attachment end of the interarch device avoid the unwanted movement of the end of the device into the patient's bite. For example, the telescoping body of a device may be replaced by a simple, non-telescoping rod which will apply a force between the attached dental appliances. This adaptation of the invention would have the same beneficial effect without providing the telescoping function. Also, the hook or loop type attachment means may be replaced by a corkscrew-like helical structure at the end of the pushrod to achieve the desired pivotable and slidable attachment to the archwire. Other modifications may be made which will be obvious to one of skill in the art from the description of the preferred embodiment, however the scope of the applicant's invention should be limited only by the following claims and their legal equivalents.

What is claimed is:

1. An interarch telescoping orthodontic device for a person, comprising:

a body including a cylinder having first attachment means for affixing to an upper tooth at one end and an opening at an opposite end;

a telescoping rod having one end slidably retained within a bore of said cylinder and an opposite end extending from said open end of said cylinder and including second attachment means;

said second attachment means for providing a pivotable hook attachment about an archwire affixed to an orthodontic appliance affixed to a lower tooth; and a recurve bend located on said rod adjacent said opposite end such that when the person's jaws are moved toward the closed position, contact between the sides of the hook and the archwire hold the rod away from the person's bite.

2. An interarch orthodontic device comprising:

a rod having a posterior end with first attachment means for rotatable affixation of said rod to a dental appliance affixed to a tooth of a person's upper arch;

second attachment means at an anterior end of said rod for providing a pivotable hook attachment about an archwire affixed to an orthodontic appliance affixed to a tooth on the patient's lower arch; and a recurve bend located on said rod adjacent said second attachment means such that when the patient's jaws are moved toward the closed position, contact between the sides of the hook and the archwire hold the rod away from the person's bite.

3. The orthodontic device of claim 1 further including spring means located within said cylinder bore providing a resilient force bearing against said one end of said rod.

4. The orthodontic device of claim 1 wherein said recurve bend is greater than 135 degrees.

5. The orthodontic device of claim 3 wherein the posterior end of said rod includes a substantially cylindrical cavity which receives said spring means.

6. The interarch orthodontic device of claim 1 wherein the second attachment means is anterior to the first attachment means.

7. The interarch orthodontic device of claim 1 wherein the second attachment means is posterior to the first attachment means.

8. The orthodontic device of claim 1 further including spring means located coaxial with and surrounding said cylinder and said rod providing a resilient force between the ends of said device.

9. The orthodontic device of claim 1 further including an offset bend in the lateral plane.

10. The orthodontic device of claim 1 wherein said second attachment means is a loop.

11. The orthodontic device of claim 1 wherein said recurve bend is approximately 270 degrees such that the pivot point of the second attachment means lies below the axis of the body of the interarch device in the vertical plane.

* * * * *